United States Patent
Körber et al.

(12)

(10) Patent No.: US 11,491,438 B2
(45) Date of Patent: Nov. 8, 2022

(54) OXYGEN CONCENTRATOR SYSTEM AND METHOD FOR OPERATING THE SAME

(71) Applicant: KONINKLIJKE PHILIPS N.V., Eindhoven (NL)

(72) Inventors: Achim Körber, Eindhoven (NL); Rainer Hilbig, Eindhoven (NL); Paul van der Sluis, Eindhoven (NL); Douglas Adam Whitcher, Monroeville, PA (US); Brian Edward Dickerson, Kennesaw, GA (US); Daniel Paul Servansky, Monroeville, PA (US)

(73) Assignee: Koninklijke Philips N.V., Eindhoven (NL)

( * ) Notice: Subject to any disclaimer, the term of this patent is extended or adjusted under 35 U.S.C. 154(b) by 219 days.

(21) Appl. No.: 17/092,400

(22) Filed: Nov. 9, 2020

(65) Prior Publication Data

US 2021/0229026 A1   Jul. 29, 2021

Related U.S. Application Data

(60) Provisional application No. 62/966,608, filed on Jan. 28, 2020.

(51) Int. Cl.
  *B01D 53/047* (2006.01)
  *B01D 53/04* (2006.01)

(52) U.S. Cl.
  CPC ....... *B01D 53/047* (2013.01); *B01D 53/0446* (2013.01); *B01D 2256/12* (2013.01);
  (Continued)

(58) Field of Classification Search
  CPC .......... B01D 2256/12; B01D 2257/102; B01D 2259/40009; B01D 2259/402;
  (Continued)

(56) References Cited

U.S. PATENT DOCUMENTS 6,277,174 B1   8/2001   Neu et al.
6,691,702 B2   2/2004   Appel
(Continued)

FOREIGN PATENT DOCUMENTS

CA    2369949 A1    8/2003
CN    103418208 B   12/2013

OTHER PUBLICATIONS

International Search Report for PCT/EP2021/051631 filed Jan. 25, 2021.
(Continued)

*Primary Examiner* — Sharon Pregler
(74) *Attorney, Agent, or Firm* — Daniel H. Brean

(57) ABSTRACT

Provided is a system for adsorbing a gaseous component comprising nitrogen from a pressurized flow of air containing the gaseous component. The system comprises a first adsorption bed, and a second adsorption bed. Each of the adsorption beds are suitable for selectively adsorbing the gaseous component from the flow of air to produce a product gas having a higher oxygen concentration than that of the air. The system includes an adjustable feed gas supply which alternately supplies the first adsorption bed and the second adsorption bed with the air. The first adsorption bed is supplied with air during a first half cycle of operation of the system, and the second adsorption bed is then supplied with air during a second half cycle of operation of the system. The feed gas supply enables adjustment of at least one parameter relating to the amount or respective amounts of air being supplied to the first adsorption bed in the first half cycle and/or to the second adsorption bed in the second half cycle. A connection and valve assembly is provided between the first and second adsorption beds. The connection and valve assembly diverts a portion of the product gas, produced from the respective absorption bed being supplied with the flow of air during the respective half cycle, to the other adsorption
(Continued)

bed. This causes previously adsorbed gaseous component to be released from latter. The released gaseous component then escapes from the system, e.g. to the atmosphere, via a vent. A sensor system determines a measure of the flow rate of waste gas, including the released gaseous component, escaping from the system via the vent. The at least one parameter can be adjusted based on the measure in order to tune the performance of the system. Further provided is a method for operating the system.

15 Claims, 9 Drawing Sheets

(52) U.S. Cl.
CPC .. *B01D 2257/102* (2013.01); *B01D 2259/402* (2013.01); *B01D 2259/40009* (2013.01)

(58) Field of Classification Search
CPC .... B01D 2259/4533; B01D 2259/4541; B01D 53/0407; B01D 53/0446; B01D 53/047; B01D 53/053
See application file for complete search history.

(56) References Cited

U.S. PATENT DOCUMENTS

| | | |
|---|---|---|
| 7,234,450 B1 | 6/2007 | Amano et al. |
| 7,329,304 B2 | 2/2008 | Bliss |
| 7,445,663 B1 | 11/2008 | Frola |
| 7,722,698 B2 | 5/2010 | Chekal et al. |
| 9,278,185 B2 | 3/2016 | Edwards et al. |
| 9,649,589 B2 | 5/2017 | Kothare |
| 9,873,078 B2 | 1/2018 | Hilbig et al. |
| 9,907,926 B2 * | 3/2018 | Allum ................. A61M 16/209 |
| 2002/0121191 A1 | 9/2002 | Warren |
| 2006/0288869 A1 | 12/2006 | Hiscock |

OTHER PUBLICATIONS

Doong, S.J. et al., "Effect of operation symmetry on pressure swing adsorption process"; Adsorption, 4: 149-158, 1998.

Lu, Y. et al., "Tuning of pressure swing adsorption systems based on differential pressure profile". Adsorption, 11: 315-324, 2005.

* cited by examiner

OXYGEN CONCENTRATOR SYSTEM AND METHOD FOR OPERATING THE SAME

CROSS-REFERENCE TO RELATED APPLICATIONS

This patent application claims the priority benefit under 35 U.S.C. § 119(e) of U.S. Provisional Application No. 62/966,608 filed on Jan. 28, 2020, the contents of which are herein incorporated by reference.

FIELD OF THE INVENTION

The present invention relates to a system for adsorbing a gaseous component from a pressurized flow of feed gas containing the gaseous component, and particularly an oxygen concentrator system which adsorbs nitrogen from a pressurized flow of air. The present invention further relates to a method for operating the system.

BACKGROUND OF THE INVENTION

Pressure swing adsorption (PSA) systems are employed for separating the gaseous components of gas mixtures, such as for separating the gaseous components of air. Oxygen concentrator systems are known for separating nitrogen from ambient air, and delivering a stream of oxygen-enriched gas that may be stored in a tank and/or delivered to a patient requiring supplemental oxygen.

Portable oxygen concentrator (POC) systems have been employed for improving the comfort and quality of life of patients suffering from various lung diseases. POC systems have the advantage that supplemental oxygen can be supplied to the patient without the requirement for the patient to be supplied with purified oxygen from an oxygen cylinder, which can be large and heavy. The POC system may therefore assist to improve the patient's mobility.

FIG. 1 depicts a simplified process flow diagram of a prior art POC system 100. The system 100 comprises a feed gas supply 102 which alternately supplies a flow of pressurized air to a first adsorption bed 104 and a second adsorption bed 106. The flow of pressurized air is generated in this case by a compressor 108, which may be included in the feed gas supply 102. The feed gas supply 102 further comprises a feed valve arrangement 110, 112 including a first feed valve 110 and a second feed valve 112. Supply of the pressurized air alternates between the respective adsorption beds 104, 106 by the first feed valve 110 being closed and the second feed valve 112 being open, followed by the second feed valve 112 being closed and the first feed valve 110 being open, and so on.

Each of the first and second adsorption beds 104, 106 adsorbs nitrogen from the pressurized flow of air being supplied thereto by the feed gas supply 102. An oxygen-enriched product gas (e.g. having an oxygen concentration of >89%) flows out of a downstream end of the respective adsorption bed 104, 106, having passed through a suitable adsorbent material. In the case of a POC, a suitable nitrogen-adsorbing material, e.g. zeolite pellets, is included in the adsorption beds 104, 106.

The majority of the product gas leaving the first adsorbent bed 104 passes through a first check valve 114A to a storage tank 116 and/or towards a patient via a delivery valve 118. The arrow 120 may be regarded as representing delivery of the product gas to the patient, e.g. via a suitable respiratory circuit (not visible in FIG. 1). Similarly, the majority of the product gas leaving the second adsorbent bed 106 passes through a second check valve 114B on its way to the storage tank 116 and/or the patient.

The POC system 100 further comprises a connection and valve assembly 122 between the first adsorption bed 104 and the second adsorption bed 106. The connection and valve assembly 122 diverts a portion of the product gas, which is produced by one of the respective adsorption beds 104, 106 being supplied with the flow of feed gas, to and through the other adsorption bed 106, 104, thereby releasing previously adsorbed nitrogen. The diverted product gas thus regenerates the respective adsorption bed 106, 104 to which it is supplied at relatively low pressure, e.g. close to ambient pressure.

As shown in FIG. 1, the connection and valve assembly 122 comprises a purge orifice 124 which delivers part of the product gas flow from one of the respective adsorption beds 104, 106 to the other adsorption bed 106, 104.

The waste gas including the nitrogen released from the first adsorption bed 104, when it is being regenerated, is vented into the atmosphere via a first exhaust valve 126A. Similarly, the waste gas including the nitrogen released from the second adsorption bed 106, when it is being regenerated, is vented into the atmosphere via a second exhaust valve 126B. Venting of the waste gas from the system 100 is represented in FIG. 1 by the arrows 127A, 127B.

The connection and valve assembly 122 may also comprise an equalization valve arrangement 128 configured to transfer pressure from one of the respective adsorption beds 104, 106 which is pressurized to the other adsorption bed 106, 104 prior to the feed gas supply 102 switching to supply the feed gas to the other adsorption bed 106, 104.

Whilst POC systems, such as the POC system 100 depicted in FIG. 1, have been found to operate effectively, it is desirable to improve the performance of such systems, as well as the performance of PSA systems more generally. In particular, it remains a challenge to improve the capability of such systems to maintain production of relatively high purity product gas. It would also be desirable to produce relatively high purity product gas whilst operating the system with reduced energy consumption.

SUMMARY OF THE INVENTION

The invention is defined by the claims.

According to an aspect there is provided an oxygen concentrator system for adsorbing a gaseous component comprising nitrogen from a pressurized flow of air containing the gaseous component, the system comprising: a first adsorption bed; a second adsorption bed, each of the first and second adsorption beds being for selectively adsorbing the gaseous component from the flow of air to produce a product gas having a higher oxygen concentration than that of the air; a feed gas supply configured to supply the flow of air alternately to the first adsorption bed and the second adsorption bed, the feed gas supply being adjustable such as to enable adjustment of at least one parameter relating to an amount of air being alternately supplied to the first adsorption bed and/or to the second adsorption bed; a connection and valve assembly between the first and second adsorption beds, the connection and valve assembly being configured such that a portion of the product gas, produced from the respective absorption bed being supplied with the flow of air, is supplied to the other adsorption bed thereby to release adsorbed gaseous component from the other adsorption bed; a vent for venting waste gas including the released gaseous component from the system; and a sensor system comprising a sensor in fluid communication with the waste gas, the sensor system being configured to determine a measure relating to a flow rate of the waste gas being vented from the system via the vent.

The term "selectively adsorbing the gaseous component" may mean that, under the conditions in the respective adsorption bed when the pressurized flow of air is being supplied thereto, the gaseous component is predominantly adsorbed by the respective adsorption bed in preference to the oxygen present in the air.

The present disclosure is based on the realization that a sensor system for determining a measure relating to a flow rate of vented waste gas, deriving from one of the respective adsorption beds, may facilitate process control of a system in which the feed gas supply is adjustable so as to permit adjustment of at least one parameter relating to an amount of air being supplied to one or both of the adsorption beds. This is because the flow rate of waste gas may act as a convenient and responsive proxy for the adsorption capacity of the respective adsorption bed from which the waste gas derives.

In particular, the measure may respond relatively rapidly to changes in the system, e.g. relative to other measurable factors such as product purity. Such rapid response may, for example, enable efficient tuning of the operation of the system.

For example, an asymmetry in the adsorption capacities of the respective adsorption beds may, for example, be straightforwardly detected and quantified using the sensor system, and the feed gas supply may be adjusted to remove or lessen the asymmetry, which may in turn improve the purification/separation performance of the system.

The system may comprise a controller for controlling the feed gas supply, the controller being configured to: receive the measure from the sensor system; and adjust the at least one parameter based on the measure. In this manner, the controller may enable the system to respond automatically to the measure obtained via the sensor system. The system may thus respond relatively quickly, without the requirement for user intervention, to any changes in the amount of waste gas being produced by the respective adsorption beds.

The controller may, for example, be configured to, based on the measure, adjust the at least one parameter from a predetermined initial setting. The initial setting may, for instance, assume that the first and second adsorption beds have the same adsorption capacity. The system as supplied may be initially configured to operate relatively close to its operating settings, but the system may automatically adjust to the operating settings in use by taking account of the measure received from the sensor system.

Whilst automatic control over the system may be preferred, the system, and in particular the feed gas supply, may be alternatively or additionally adjustable via user intervention. In this respect, the system may, for example, include a suitable user interface which enables the user to view the measure taken by the sensor system and adjust the feed gas supply accordingly.

The at least one parameter may comprise a first time period during which the feed gas supply supplies the flow of air to the first adsorption bed. The at least one parameter may alternatively or additionally comprise a second time period during which the feed gas supply supplies the flow of air to the second adsorption bed.

The flow rate of air supplied to the first adsorption bed may, for example, remain substantially constant, such that adjusting the feed gas supply to lengthen the first time period may result in relatively more, e.g. a greater volume, of the air being supplied to the first adsorption bed. Conversely, adjusting the feed gas supply such that the first time period is made shorter may result in relatively less, e.g. a lower volume, of the air being supplied to the first adsorption bed. Similar considerations apply to the second adsorption bed. The respective time period may, for example, be adjusted according to the measure, since the latter is indicative of the adsorption capacity of the respective adsorption bed.

In embodiments wherein the system includes the controller, the controller may be configured to adjust the first time period and the second time period such that substantially the same volume of waste gas is vented when the first adsorption bed is supplied by the feed gas supply during the first time period as when the second adsorption bed is supplied by the feed gas supply during the second time period.

The term "substantially the same volume" in this context may mean that the percentage difference of the waste gas volume released from the first adsorption bed and the waste gas released from the second adsorption bed is less than or equal to 5%, such as less than or equal to 1%. This percentage difference may be calculated by dividing the difference between the respective waste gas volumes by the average of the two waste gas volumes (and multiplying the result by 100).

It has been surprisingly found that enhanced performance of the system may be attained by adjusting the difference between the first and second feed times such that determined waste gas volumes of both adsorption beds are substantially the same as each other. When, for instance, the respective adsorption capacities of the first and second adsorption beds are exactly the same as each other, the system may be operated such that the determined waste gas volumes are exactly the same as each other. In practice, however, a relatively small difference in adsorption capacity may exist between the respective adsorption beds (e.g. a percentage difference of up to 20%), and in this case, the system may be operated such as to produce waste gas volumes from the respective adsorption beds with a corresponding relatively small difference in the waste gas volumes produced by the respective adsorption beds.

Because sensing the measure via the sensor system may enable the system to respond relatively quickly in order to adjust the first and second time periods, tuning the performance of the system according to the measure may be particularly effective. By comparison, monitoring, for instance, the product purity downstream of the respective adsorption beds may entail a longer response time.

The at least one parameter may comprise a feed gas flow rate of the air being supplied to the respective adsorption beds by the feed gas supply. By adjusting the feed gas supply to supply a higher or lower feed gas flow rate, an increased or decreased amount, e.g. volume, of the air may be supplied to the respective adsorption bed.

When, for example, the feed gas supply comprises a compressor, higher or lower feed gas flow rates may be attained by increasing or decreasing the compressor speed. Optimizing the compressor speed according to the measure of the flow rate of waste gas being vented from the system may have the additional benefit of improving, i.e. decreasing, the energy consumption of the system.

In an embodiment, the sensor comprises a differential pressure sensor. Differential pressure sensors may be inexpensive, accurate, and have sufficient sensitivity in order to provide a reliable measure of the waste gas flow rate. The differential pressure sensor may, for example, have a sensing range from 0 to 15 psig (103420 Pa), and/or a resolution of at least 12 bit.

The vent may be defined by one or more exhaust orifice. The number and diameter of the exhaust orifice(s) may enable tuning of the flow rate of the waste gas escaping from the vent, e.g. according to the design of the sensor system, including the sensor.

Each of the one or more exhaust orifice may, for example, have a diameter in the range of 1 mm to 5.5 mm. An orifice diameter greater than or equal to 1 mm may assist to avoid an excessively high pressure drop, which would otherwise hamper the venting of the waste gas, e.g. into the atmosphere. On the other hand, an orifice diameter which is less than or equal to 5.5 mm may assist to minimize the risk that the measurement accuracy of the sensor is compromised. A diameter within the above ranges may also be suitable for the dimensions, flow/pressure characteristics, etc. of a typical portable oxygen concentrator (POC) system.

The connection and valve assembly may comprise an equalization valve arrangement configured to transfer pressure from one of the respective adsorption beds which is pressurized to the other adsorption bed prior to the feed gas supply switching to supply the air to the other adsorption bed. The equalization valve arrangement may relatively rapidly bring the first and second adsorption beds to the same pressure prior to the feed gas supply switching the respective adsorption bed to which the feed gas is supplied.

The system may further comprise a conduit arranged to carry the product gas downstream away from the first and second adsorption beds. In some examples, the system comprises a storage tank for receiving the product gas carried via the conduit and storing the product gas.

The first adsorption bed may have a first adsorption capacity for the gaseous component, and the second adsorption bed may have a second adsorption capacity for the gaseous component. The percentage difference between the first adsorption capacity and the second adsorption capacity may be less than or equal to 20%, the respective adsorption capacities being measured under the same conditions. The first and second adsorption capacities may, for example, be calculated from the experimental breakthrough curves. The percentage difference may be calculated by dividing the difference between the respective adsorption capacities by the average of the two waste adsorption capacities (and multiplying the result by 100).

The first adsorption bed may comprise a first port and the second adsorption bed may comprise a second port. The feed gas supply may be configured to supply the flow of air alternately to the first port and the second port.

The first adsorption bed may comprise a further first port spaced apart from the first port across the first adsorption bed, and the second adsorption bed may comprise a further second port spaced apart from the second port across the second adsorption bed, the product gas being released from the first adsorption bed and the second adsorption bed via the further first port and the further second port respectively. In such an embodiment, the connection and valve assembly may be configured such that the portion of the product gas is passed from one of the respective further first and further second ports to the other of the respective further second and further first ports.

Such a configuration, in which the portion of the product gas is supplied to the respective further port at the downstream end of the respective adsorption bed may result in efficient regeneration, e.g. in comparison to the scenario in which the portion of product gas is supplied to an upstream port of the respective adsorption bed.

In an embodiment, the system is a portable oxygen concentrator system. Such a portable oxygen concentrator system may, for example, be dimensioned and sufficiently lightweight to be carried by the subject and/or a care provider between different locations.

According to a further aspect there is provided a method for operating an oxygen concentrator system for adsorbing a gaseous component comprising nitrogen from a pressurized flow of air containing the gaseous component, the system comprising: a first adsorption bed; a second adsorption bed; a feed gas supply configured to supply the flow of air alternately to the first adsorption bed and the second adsorption bed; a connection and valve assembly between the first and second adsorption beds; a vent for venting waste gas from the system; and a sensor system, the method comprising: controlling the feed gas supply to supply the flow of air to the first adsorption bed, the first adsorption bed selectively adsorbing the gaseous component from the supplied air to produce a product gas having a higher oxygen concentration than that of the air; controlling the valve assembly such that a portion of the product gas produced from the first absorption bed is supplied to the second adsorption bed thereby to release adsorbed gaseous component from the second adsorption bed, the released gaseous component being vented from the system in the waste gas; using the sensor system to determine, from the vented waste gas, a measure relating to a flow rate of the waste gas escaping from the system via the vent; and adjusting at least one parameter relating to an amount of air being supplied to the first adsorption bed and/or the second adsorption bed based on the measure.

BRIEF DESCRIPTION OF THE DRAWINGS

Examples of the invention will now be described in detail with reference to the accompanying drawings, in which.

DETAILED DESCRIPTION OF THE EMBODIMENTS

Figure 1:
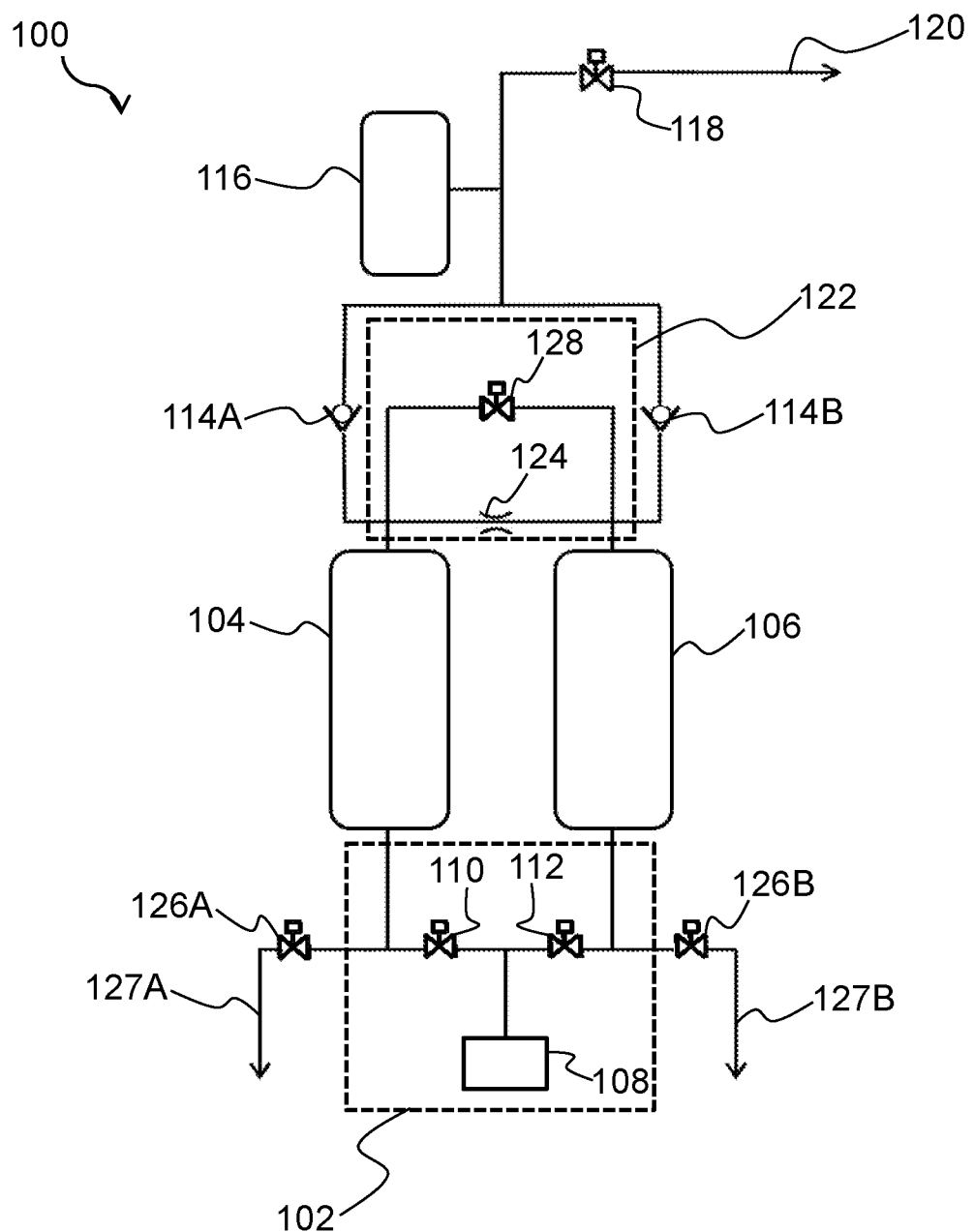
FIG. 1 depicts a simplified process flow diagram of a prior art portable oxygen concentrator system.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

Provided is an oxygen concentrator system for adsorbing a gaseous component comprising nitrogen from a pressurized flow of air containing the gaseous component. The system comprises a first adsorption bed, and a second adsorption bed. Each of the adsorption beds are suitable for selectively adsorbing the gaseous component from the flow of air to produce a product gas having a higher oxygen concentration than that of the air. The system includes an adjustable feed gas supply which alternately supplies the first adsorption bed and the second adsorption bed with the air. The first adsorption bed is supplied with air during a first half cycle of operation of the system, and the second adsorption bed is then supplied with air during a second half cycle of operation of the system. The feed gas supply enables adjustment of at least one parameter relating to the amount or respective amounts of air being supplied to the first adsorption bed in the first half cycle and/or to the second adsorption bed in the second half cycle. A connection and valve assembly is provided between the first and second adsorption beds. The connection and valve assembly diverts a portion of the product gas, produced from the respective absorption bed being supplied with the flow of air during the respective half cycle, to the other adsorption bed. This causes previously adsorbed gaseous component to be released from latter. The released gaseous component then escapes from the system, e.g. to the atmosphere, via a vent. A sensor system determines a measure of the flow rate of waste gas, including the released gaseous component, escaping from the system via the vent. The at least one parameter can be adjusted based on the measure in order to tune the performance of the system. Further provided is a method for operating the system.

The pressure swing adsorption (PSA) cycle in a gas separation/purification system, such as a portable oxygen concentrator (POC), may be tuned in order to optimize performance by symmetrizing the operation of a pair of adsorption beds. In practice, however, this symmetrizing may be hampered by the respective adsorption capacities of the two adsorption beds being slightly different from each other.

S. J. Doong and P. Propsner in "Effect of operation symmetry on pressure swing adsorption process"; Adsorption, 4: 149-158, 1998, disclose that, in the case of large-scale PSA systems, asymmetrical operation may cause drastically different temperature profiles in the respective adsorption beds, hence poorer performance. The importance of maintaining operation symmetry in PSA processes is emphasized in this paper.

Y. Lu, S.-J. Doong, and M. Buelow in "Tuning of pressure swing adsorption systems based on differential pressure profile". Adsorption, 11: 315-324, 2005 describe how the adsorption bed pressure profile may be used as an indicator of any imbalance between the respective adsorption beds. It may, however, be difficult to detect any symmetry problem in operation of the system from such pressure profiles alone.

Moreover, the bed pressure may not be sensitive enough to reflect any imbalance of the PSA system, and may thus have limited utility for plant tuning and process control. Other factors, such as product purity and bed temperature may be slow to respond to any changes in the system.

Whilst adjustment of the difference in the respective time periods during which the first and second adsorption beds of the system are supplied with the feed gas may assist to optimize the system for higher product purity, the product purity may react relatively slowly (e.g. in the order of about 10 minutes for a typical POC system) to changes in the PSA parameters, as described by Lu et al. Furthermore, monitoring only the product purity may not indicate which of the pair of adsorption beds has higher adsorption capacity than the other. As such, monitoring the product purity may not assist to designate, within a suitable period of time, which of the respective adsorption beds should be operated with a longer feed time relative to the other adsorption bed.

Therefore, a system and method which enables relatively rapid quantification of an asymmetry of the PSA process would be highly desirable.

The present disclosure is based on the realization that a sensor system for determining a measure relating to a flow rate of vented waste gas, deriving from one of the respective adsorption beds, may facilitate process control of a system in which the feed gas supply is adjustable so as to permit adjustment of at least one parameter relating to an amount of feed gas being supplied to one or both of the adsorption beds. This is because the flow rate of waste gas may act as a convenient and responsive proxy for the adsorption capacity of the respective adsorption bed from which the waste gas derives.

In particular, the measure may respond relatively rapidly to changes in the system, e.g. relative to other measurable factors such as product purity. Such rapid response may, for example, enable efficient tuning of the operation of the system.

For example, an asymmetry in the adsorption capacities of the respective adsorption beds may, for example, be straightforwardly detected and quantified using the sensor system, and the feed gas supply may be adjusted to remove or lessen the asymmetry, which may in turn improve the purification/separation performance of the system.

Figure 2:
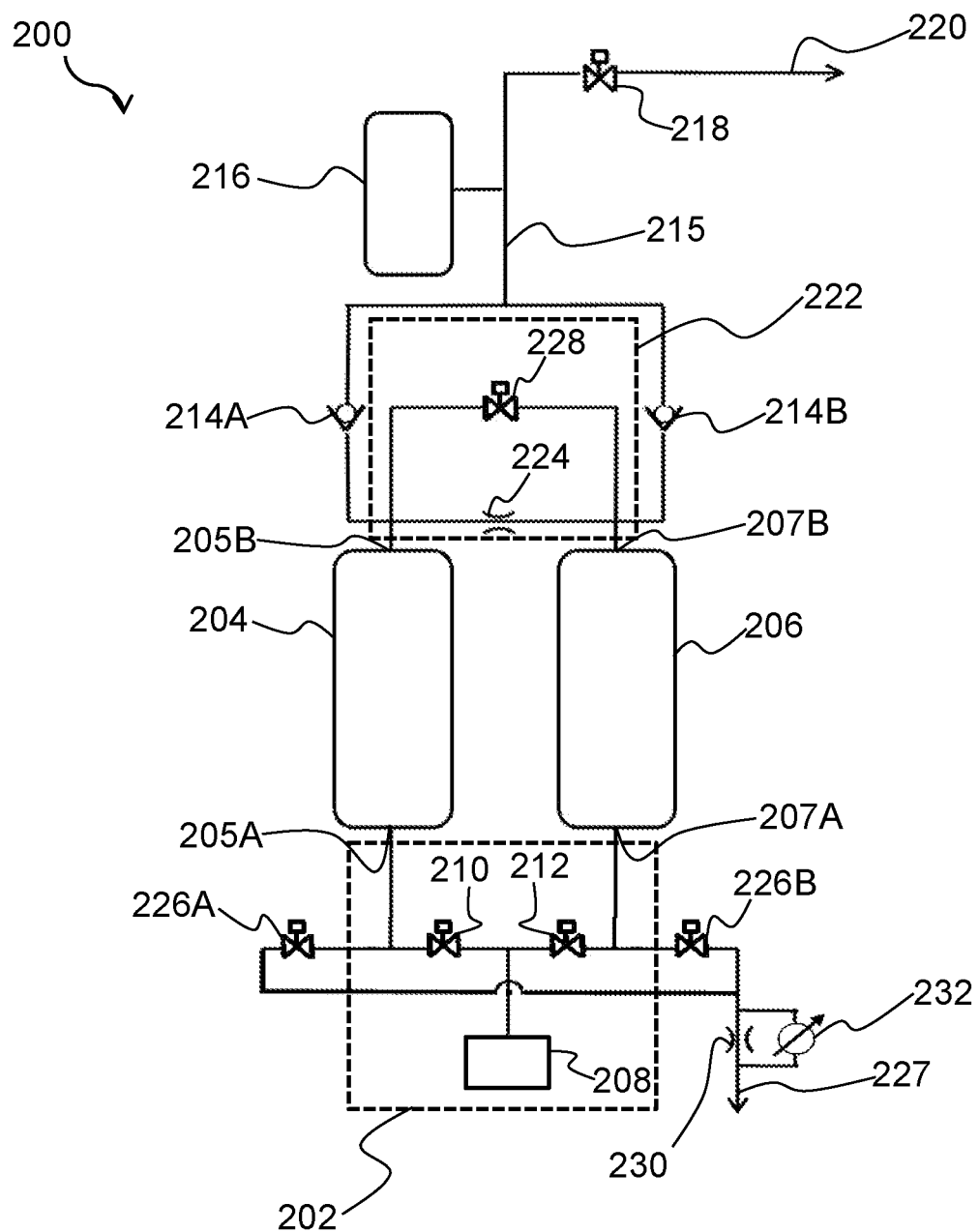
FIG. 2 depicts a simplified process flow diagram of a system according to an example.

FIG. 2 depicts a simplified process flow diagram of a system 200 according to an example. The system 200 comprises a feed gas supply 202 which alternately supplies a flow of pressurized air to a first adsorption bed 204 and a second adsorption bed 206.

In the example shown in FIG. 2, the feed gas supply 202 comprises a source of pressurized gas 208. The feed gas supply 202 further comprises a feed valve arrangement 210, 212 including a first feed valve 210 and a second feed valve 212. Supply of the pressurized flow of gas alternates between the respective adsorption beds 204, 206 by the first feed valve 210 being closed and the second feed valve 212 being open, followed by the second feed valve 212 being closed and the first feed valve 210 being open, and so on. In this way, the feed gas supply 202 supplies the first adsorption bed 204 in a first half cycle of operation of the system 200, and supplies the second adsorption bed 206 in a subsequent second half cycle.

As shown in FIG. 2, the feed gas supply 202 is configured to supply the flow of feed gas alternately to a first port 205A of the first adsorption bed 204 and a second port 207A of the second adsorption bed 206. The first port 205A is positioned at an upstream end of the first adsorption bed 204. Similarly, the second port 207A is positioned at an upstream end of the second adsorption bed 206.

The first and second feed valves 210, 212 may, for example, be powered valves, e.g. solenoid valves. The first and second feed valves 210, 212 may be controlled, for instance, by a controller, such as a microcontroller (not visible in FIG. 2).

The feed gas supply 202 is adjustable in that the feed gas supply 202 permits adjustment of at least one parameter relating to the amount or respective amounts of feed gas being supplied to the first adsorption bed 204 in the first half cycle and/or to the second adsorption bed 206 in the second half cycle.

The at least one parameter may, for example, comprise a first time period during which the feed gas supply 202 supplies the flow of feed gas to the first adsorption bed 204. The flow rate of feed gas supplied to the first adsorption bed 204 may, for example, remain constant, such that adjusting the feed gas supply 202 to lengthen the first time period may result in relatively more, e.g. a greater volume, of the feed gas being supplied to the first adsorption bed 204. Conversely, adjusting the feed gas supply 202 such that the first time period is made shorter may result in relatively less, e.g. a lower volume, of the feed gas being supplied to the first adsorption bed 204.

The first time period may be adjusted according to a measure of a flow rate of the waste gas being vented from the system 200 during regeneration of the first adsorption bed 204, as will be described in greater detail herein below.

The at least one parameter may alternatively or additionally comprise a second time period during which the feed gas supply 202 supplies the flow of feed gas to the second adsorption bed 206. The second time period may be adjusted according to the measure of a flow rate of waste gas being vented from the system 200 during regeneration of the second adsorption bed 206, as will also be described in greater detail herein below.

Adjusting the respective time periods may, for example, be achieved by adjusting the timings in the control sequence employed by the controller (not visible in FIG. 2) which determine when the first and second feed valves 210, 212 are opened and closed.

The at least one parameter may alternatively or additionally comprise a feed gas flow rate of the feed gas being supplied to the respective adsorption beds 204, 206 by the feed gas supply 202. By adjusting the feed gas supply 202 to supply a higher or lower feed gas flow rate, an increased or decreased amount, e.g. volume, of the feed gas may be supplied to the respective adsorption bed 204, 206 in a given time period.

When, for example, the feed gas supply 202 comprises a compressor as the source of pressurized feed gas 208, higher or lower feed gas flow rates may be attained by increasing or decreasing the compressor speed. Optimizing the compressor speed according to the measure of the flow rate of waste gas being vented from the system 200 may have the additional benefit of improving, i.e. decreasing, the energy consumption of the system 200. It is nevertheless noted that alternative ways of adjusting the feed gas flow rate, e.g. using a suitable flow control valve, will also be immediately apparent to the skilled person.

Each of the adsorption beds 204, 206 are suitable for selectively adsorbing the gaseous component from the flow of feed gas to produce a product gas. The adsorption beds 204, 206 may be packed with a suitable adsorbent material for adsorbing the target gaseous component. Adsorbent materials are known for selectively adsorbing various gases present in feed gas mixtures. For example, a suitable adsorbent material for adsorbing nitrogen from a flow of pressurized air may comprise or be a zeolite, e.g. in pellet form. Various suitable zeolites are known for use in a POC system, such as synthetic zeolites, e.g. OXYSIV™ 5 (Honeywell UOP), OXYSIV™ 5A (Honeywell UOP), OXYSIV™ MDX (Honeywell UOP), Z10-06 molecular sieves from Zeochem, "Nitroxy Revolution", "Nitroxy SXSDM" and/or "Nitroxy Efficiency" from Arkema (CECA).

In an embodiment, the percentage difference between the first adsorption capacity of the first adsorption bed 204 and the second adsorption capacity of the second adsorption bed 206 is less than or equal to 20%, the respective adsorption capacities being measured under the same conditions. The first and second adsorption capacities may, for example, be calculated from the experimental breakthrough curves.

In practice, this may mean that the dimensions and packing of the respective adsorption beds 204, 206 may be substantially the same, as schematically depicted in FIG. 2. This may assist to enable symmetrical operation of the system 200, which may be desirable in terms of optimizing the performance of the system 200. Moreover, adjustment of the at least one parameter may be facilitated when the respective adsorption capacities of the first and second adsorption beds 204, 206 are relatively close to each other (e.g. when the percentage difference between the first and second adsorption capacities is less than or equal to 20%).

The first adsorption bed 204 may comprise a further first port 205B positioned at a downstream end of the first adsorption bed 204. Thus, the pressurized flow of air may enter the first adsorption bed 204 via the first port 205A, and pass through the adsorbent material packed therein which causes adsorption of the gaseous component. The product gas, having a lower concentration of the gaseous component than that of the air, may then exit the first adsorption bed 204 via the further first port 205B.

Similarly, the second adsorption bed 206 may comprise a further second port 207B positioned at a downstream end of the second adsorption bed 206. Upon switching of the feed gas supply 202 to supply the second adsorption bed 206 in the second half cycle, the pressurized flow of air may enter the second adsorption bed 206 via the second port 207A, and pass through the adsorbent material packed therein. The product gas may then exit the second adsorption bed 206 via the further second port 207B.

The majority of the product gas leaving the first adsorbent bed 204 via the further first port 205B during the first half cycle may pass through a first check valve 214A, and be carried downstream via a conduit 215. In the non-limiting example shown in FIG. 2, the system 200 includes a storage tank 216 for storing the product gas for later use. The system 200 may, alternatively or additionally, comprise a delivery valve 218 for controlling the supply of product gas delivered by the system 200, as represented in FIG. 2 by the arrow 220.

Similarly, the majority of the product gas leaving the second adsorbent bed 206 via the further second port 207B during the second half cycle may pass through a second check valve 214B, and be carried downstream via the conduit 215, e.g. to the storage tank 216 and/or the delivery valve 218.

The system 200 further comprises a connection and valve assembly 222 between the first adsorption bed 204 and the second adsorption bed 206. The connection and valve assembly 222 diverts a portion of the product gas, which is produced by one of the respective adsorption beds 204, 206 being supplied with the pressurized flow of air by the feed gas supply 202 during the respective half cycle, to and through the other adsorption bed 206, 204. Previously adsorbed gaseous component is thereby released from the latter.

During the first half cycle, a portion of the product gas, produced by the first adsorption bed 204, may be supplied to the second adsorption bed 206. Similarly, during the second half cycle, a portion of the product gas, produced by the second adsorption bed 206, may be supplied to the first adsorption bed 204. In such an example, regeneration of one of the respective adsorption beds 204, 206 may occur simultaneously with product gas production by the other adsorption bed 206, 204.

The diverted product gas thus regenerates the respective adsorption bed 206, 204 to which it is supplied. The pressure of regeneration may be low in comparison to the pressure at which adsorption of the gaseous component from the air takes place. The system 200 may thus be regarded as an example of a pressure swing adsorption (PSA) system. The regeneration may, for example, be implemented using a pressure which is close to ambient pressure.

The connection and valve assembly 222 may comprise an equalization valve arrangement 228 configured to transfer pressure from one of the respective adsorption beds 204, 206 which is pressurized to the other adsorption bed 206, 204 prior to the feed gas supply 202 switching to supply the air to the other adsorption bed 206, 204. The equalization valve arrangement 228 may relatively rapidly bring both adsorption beds 204, 206 to the same pressure prior to the feed gas supply 202 switching the respective adsorption bed 204, 206 to which the air is supplied.

The connection and valve assembly 222 may comprise a purge orifice 224 which delivers the portion of the product gas flow from one of the respective adsorption beds 204, 206 to the other adsorption bed 206, 204.

As shown in FIG. 2, the connection and valve assembly 222 is configured such that the portion of the product gas is passed from one of the respective further first and further second ports 205B, 207B to the other of the respective further second and further first ports 207B, 205B. Such a configuration, in which the portion of the product gas is supplied to the downstream end of the respective adsorption bed 204, 206 may result in efficient regeneration, e.g. in comparison to the scenario in which the portion of product gas is supplied to the upstream end of the respective adsorption bed 204, 206.

The system 200 comprises a vent 230 for venting waste gas including the released gaseous component from the system 200. Venting of the waste gas from the system 200 is represented in FIG. 2 by the arrow 227. The vent 230 may, for example, vent the waste gas into the atmosphere. Venting the waste gas to the atmosphere may be safe and practical when the system 200 is employed for oxygen concentration of ambient air (provided that the system 200 is not operated within an enclosed space, as will readily be appreciated by the skilled person).

A first exhaust valve 226A may be open during the second half cycle in order to permit the waste gas to pass from the first adsorption bed 204 to the vent 230. The first exhaust valve 226A may be closed during the first half cycle.

Similarly, a second exhaust valve 226B may be open during the first half cycle in order to permit the waste gas to pass from the second adsorption bed 206 to the vent 230. The second exhaust valve 226B may be closed during the second half cycle.

The first and second exhaust valves 226A, 226B may, for example, be powered valves, e.g. solenoid valves. The first and second exhaust valves 226A, 226B may be controlled, for instance, by the controller (not visible in FIG. 2) briefly mentioned above in relation to the first and second feed valves 210, 212.

The controller may thus, for example, implement a sequence in which, the first feed valve 210 and the second exhaust valve 226B are open, and the second feed valve 212 and the first exhaust valve 226A are closed during the first half cycle, e.g. for the duration of the first time period; and the second feed valve 212 and the first exhaust valve 226A are open, and the first feed valve 210 and the second exhaust valve 226B are closed during the second half cycle, e.g. for the duration of the second time period.

As shown in FIG. 2, during the first half cycle the waste gas may pass out of the second port 207A of the second adsorption bed 206, i.e. the same (second) port 207A as that which admits the air into the second adsorption bed 206 during the second half cycle. Similarly, during the second half cycle the waste gas may pass out of the first port 205A of the first adsorption bed 204. This design may benefit from its simplicity, e.g. relative to the scenario in which air is admitted and waste gas expelled via different ports of the respective adsorption bed 204, 206.

The vent 230 may be defined by at least one exhaust orifice which serves to vent waste gas including the released gaseous component from the second adsorption bed 206 when it is being regenerated during the first half cycle, and from the first adsorption bed 204 when it is being regenerated during the second half cycle. Venting the waste gas from both of the first and second adsorption beds 204, 206 via a common exhaust orifice 230 may advantageously simplify the design of the system 200, particularly since a single sensor 233 may be employed in the sensor system 232 which determines the measure relating to a flow rate of the waste gas being vented from the system 200.

In alternative examples, the vent 230 may comprise respective exhaust orifices for venting the waste gas produced during regeneration of the first adsorption bed 204 and the second adsorption bed 206. In such examples, the sensor system 232 may include sensors 233 for sensing the waste gas escaping via the respective exhaust orifices.

Figure 3:
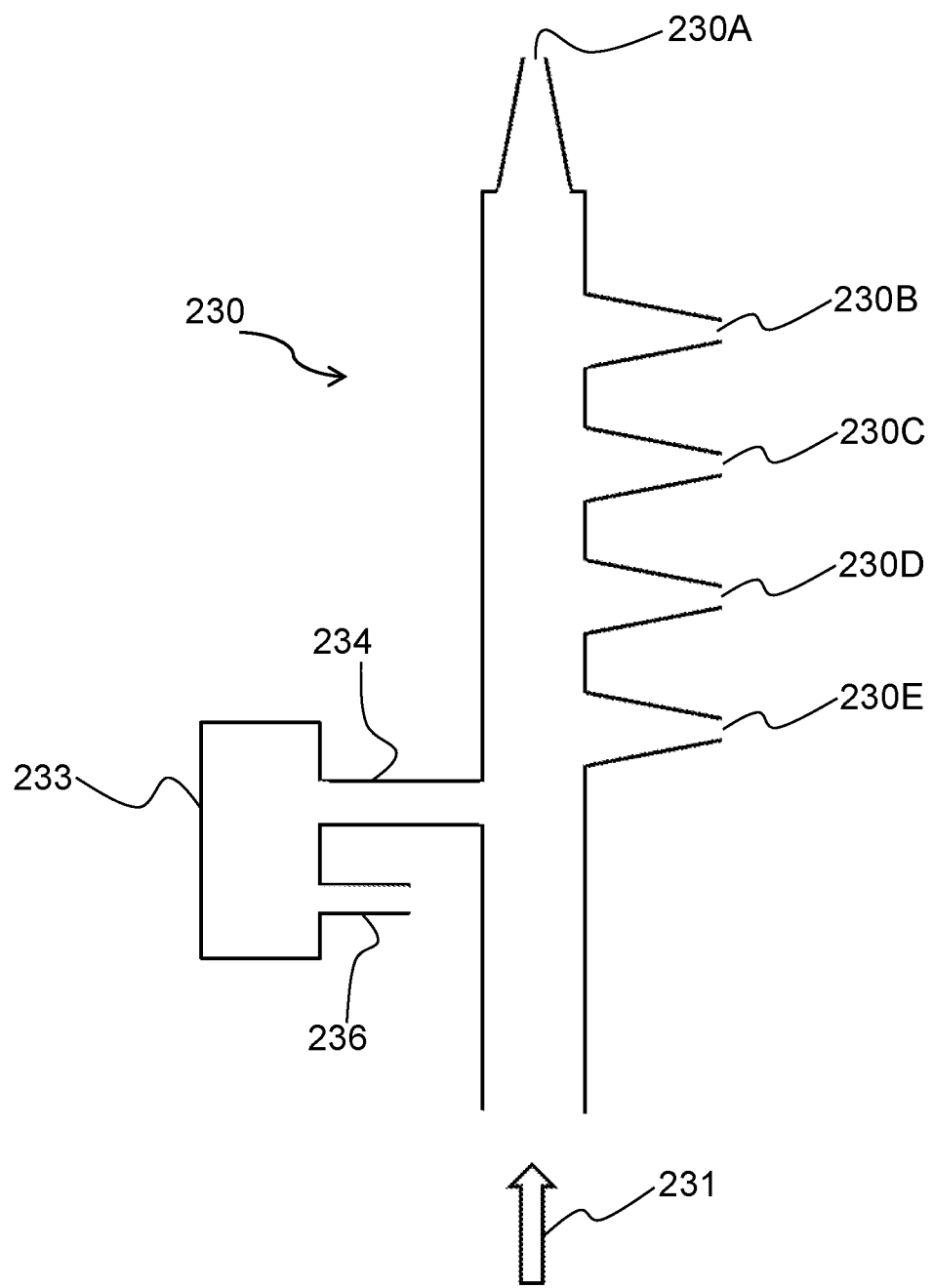
FIG. 3 schematically depicts an exemplary vent and sensor of an exemplary system.

FIG. 3 schematically depicts an exemplary vent 230 from which a flow of waste gas, as represented by the arrow 231, is vented. FIG. 3 further depicts a sensor 233 of the sensor system 232. The sensor 233 is in fluid communication with the waste gas escaping from the system 200 via the vent 230.

In an embodiment, the vent 230 is defined by at least one exhaust orifice 230A, 230B, 230C, 230D, 230E. The exemplary vent 230 shown in FIG. 3 comprises five exhaust orifices 230A, 230B, 230C, 230D, 230E from which the waste gas may escape from the system 200. Any number of exhaust orifices 230A, 230B, 230C, 230D, 230E may be employed, e.g. 1, 2, 3, 4, 5, 6, 7, 8, 9 or 10, or more. The number and diameter of the exhaust orifices 230A, 230B, 230C, 230D, 230E may enable tuning of the flow rate of the waste gas escaping from the vent 230, e.g. according to the design of the sensor system 232, including the sensor 233.

The diameter of the at least one exhaust orifice 230A, 230B, 230C, 230D, 230E may, for example, be in the range of 1 mm to 5.5 mm, e.g. 1.3 mm to 5.1 mm (or an orifice 230A, 230B, 230C, 230D, 230E dimensioned to provide an equivalent resistance to the flow of waste gas). An orifice diameter greater than or equal to 1 mm may assist to avoid an excessively high pressure drop, which would otherwise hamper the venting of the waste gas, e.g. into the atmosphere. On the other hand, an orifice diameter which is less than or equal to 5.5 mm may assist to minimize the risk that the measurement accuracy of the sensor 233 is compromised. A diameter within the above ranges may also be suitable for the dimensions, flow/pressure characteristics, etc. of a typical POC system 200.

More generally, the sensor system 232 is configured to determine a measure relating to a flow rate of the waste gas being vented from the system 200 via the vent 230. The sensor 233 may employ any suitable sensing principle provided that the sensor signals generated by the sensor 233 enable the sensor system 232 to determine the measure relating to a flow rate of the waste gas being vented.

In an embodiment, the sensor 233 comprises a differential pressure sensor. Differential pressure sensors may have sufficient sensitivity in order to provide a reliable measure of the waste gas flow rate. The differential pressure sensor may, for example, have a sensing range from 0 to 15 psig (103420 Pa), and/or a resolution of at least 12 bit.

In the non-limiting example shown in FIG. 3, the sensor 233 is fluidly connected to the waste gas via a first sensor port 234. When the sensor 233 is or comprises a differential pressure sensor, a second sensor port 236, shown in this particular example as being open to ambient pressure, provides a reference pressure.

The differential pressure sensor 233 may, for instance, enable the waste gas volume from each of the respective adsorption beds 204, 206 to be determined, as follows. The sensor system 232 may first measure the differential pressure waveform during regeneration of the respective adsorption bed 204, 206. The corresponding waste gas flow rate may then be derived from the measured or known pressure vs. flow characteristics of the exhaust orifice 230. The waste gas flow rate may be integrated to yield the waste gas volume from the respective adsorption bed 204, 206. This determination is exemplified in the non-limiting example described below with reference to FIGS. 6 and 7.

Figure 4:
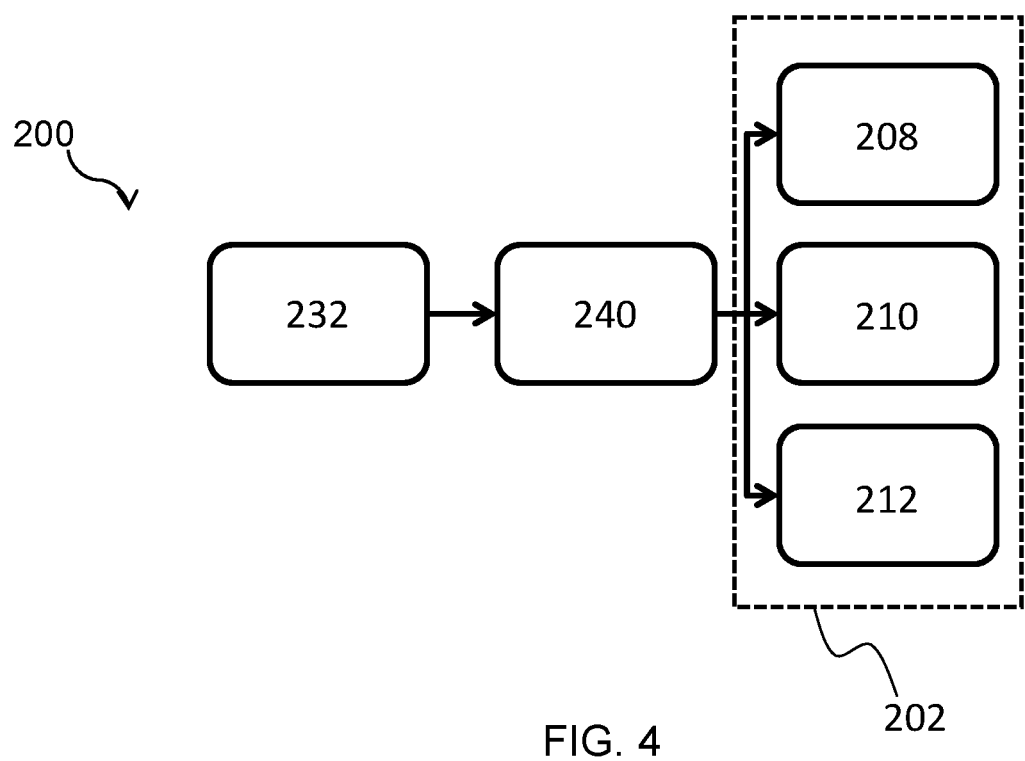
FIG. 4 shows a block diagram of part of an exemplary system.

FIG. 4 shows a block diagram of part of an exemplary system 200. In this non-limiting example, the system 200 comprises a controller 240 which receives, from the sensor system 232, the measure relating to a flow rate of the waste gas being vented from the system 200. The measure being received by the controller 240 from the sensor system 232 is represented in FIG. 4 by the arrow between the respective blocks.

The controller 240 adjusts the at least one parameter relating to an amount of air being alternately supplied to the first adsorption bed 204 and/or to the second adsorption bed 206 based on the measure. In this manner, the controller 240 may enable the system 200 to respond automatically to the measure obtained via the sensor system 232. The system 200 may thus respond relatively quickly, without the requirement for user intervention, to any changes in the amount of waste gas being produced by the respective adsorption beds 204, 206. The latter may be indicative of changes in the adsorption capacity of the respective beds.

The controller 240 may, for example, adjust the first time period and/or the second time period based on the measure. The controller 240 may thus adjust the feed gas supply 202 according to an indication of the adsorption capacity of the respective adsorption bed or beds 204, 206.

For example, should the measure be indicative of the adsorption capacity of the first adsorption bed 204 being relatively high, e.g. higher than that of the second adsorption bed 206, the controller 240 may control the feed gas supply 202 such that the first time period is longer, e.g. longer than the second time period. In this way, the system 200 may tune the amount, e.g. volume, of air being supplied to the respective adsorption bed 204, 206 based on the determined adsorption capacity of the respective adsorption bed 204, 206.

As shown in FIG. 4, the controller 240 may send control signals which control the opening/closing of the first feed valve 210 and/or the second feed valve 212 in order to control the respective time period(s), as previously described.

The controller 240 may alternatively or additionally control the source of pressurized gas 208 in order to adjust the air flow rate in response to the measure received from the sensor system 232. When, for example, the source of pressurized gas 208 includes a compressor, the controller 240 may increase or decrease the compressor speed. By adjusting the compressor speed, an increased or decreased amount, e.g. volume, of the air may be supplied to the respective adsorption bed 204, 206 in accordance with its adsorption capacity. Optimizing the compressor speed according to the measure of the flow rate of waste gas being vented from the system 200 may have the additional benefit of improving, i.e. decreasing, the energy consumption of the system 200.

In an embodiment, the system 200, including the first and second adsorption beds 204, 206 is provided with predetermined, e.g. preloaded, initial settings. Such settings may, for example, be based on calculated and/or experimentally determined performance of the system 200. This initial settings may, for instance, assume that the first and second adsorption beds 204, 206 have the same adsorption capacity.

In such an embodiment, the controller 240 may be configured to, based on the measure, adjust the at least one parameter from the predetermined initial settings. In this manner, the system 200 as supplied may be configured to operate relatively close to its operating settings, but the system 200 may automatically adjust to the operating settings in use by taking account of the measure received from the sensor system 232.

In an embodiment, the controller 240 is configured to adjust the first time period and the second time period such that substantially the same volume of waste gas is vented when the first adsorption bed 204 is supplied by the feed gas supply 202 during the first time period as when the second adsorption bed 206 is supplied by the feed gas supply 202 during the second time period. The term "substantially the same volume" in this context may mean that the percentage difference of the waste gas volume released from the first adsorption bed 204 and the waste gas released from the second adsorption bed 206 is less than or equal to 5%, such as less than or equal to 1%. This percentage difference may be calculated by dividing the difference between the respective waste gas volumes by the average of the two waste gas volumes (and multiplying the result by 100).

It has been surprisingly found that, in particular when the first and second adsorption beds 204, 206 have approximately equal adsorption capacities, e.g. having a percentage difference of less than or equal to 20%, enhanced performance of the system 200 may be attained by adjusting the difference between the first and second feed times such that determined waste gas volumes of both adsorption beds 204, 206 are substantially the same as each other. Because this technique may enable the system 200 to respond relatively quickly in order to adjust the first and second time periods, tuning the performance of the system 200 may be effectively implemented. By comparison, monitoring, for instance, the product purity downstream of the respective adsorption beds 204, 206 may entail a longer response time.

Whilst automatic control over the system 200 may be preferred, the system 200, and in particular the feed gas supply 202, may be alternatively or additionally adjustable via user intervention. In this respect, the system 200 may, for example, include a suitable user interface (not visible in FIG. 4), such as a touchscreen, a screen with surrounding buttons, etc., which enables the user to view the measure taken by the sensor system 232 and adjust the feed gas supply 202 accordingly.

In an embodiment, the controller 240 is configured to, based on the measure, detect an air leak in the system 200. This detection may, for example, be based on the gas flow balance of the system 200. A non-limiting example for providing further explanation of this embodiment is described herein below with reference to FIG. 11. The controller 240 may, for instance, control a user interface, e.g. the user interface mentioned above in relation to adjustment of the feed gas supply 202, to signal an indicator of the detected air leak. The user or caregiver may thus be prompted to have the system 200 serviced, which may involve remounting of the adsorption beds 204, 206.

In an embodiment, the system 200 is included in a portable oxygen concentrator (POC). In such an embodiment, the first and second adsorption beds 204, 206 are for selectively adsorbing nitrogen from a pressurized flow of air. In such a POC, the pressurized flow of gas is a flow of pressurized air, and the source of pressurized gas 208 may be, for example, an air compressor. An oxygen-enriched product gas (e.g. having an oxygen concentration of >89%) may flow out of a downstream end of the respective adsorption bed 204, 206.

Figure 5:
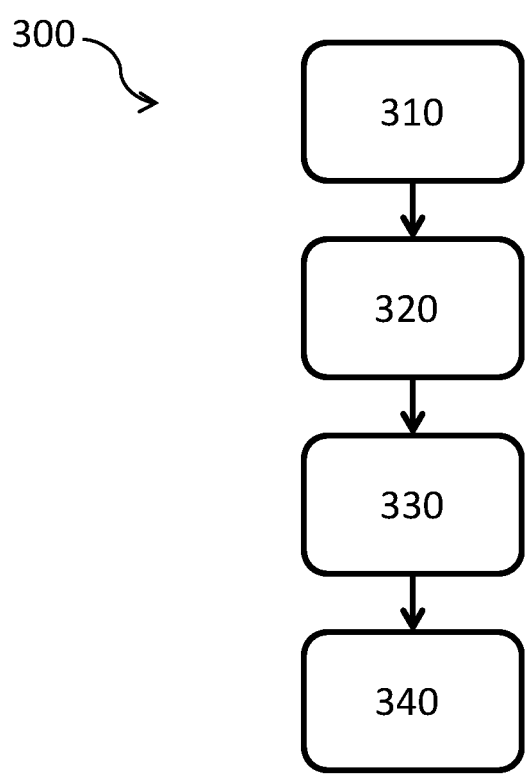
FIG. 5 shows a flowchart of a method according to an example.

FIG. 5 shows a flowchart of a method 300 according to an example. The method 300 is for operating a system for adsorbing a gaseous component from a pressurized flow of air containing the gaseous component, the system comprising: a first adsorption bed; a second adsorption bed; a feed gas supply configured to supply the flow of air alternately to the first adsorption bed and the second adsorption bed; a connection and valve assembly between the first and second adsorption beds; a vent for venting waste gas from the system; and a sensor system. The method 300 may thus, for example, involve operating the system 200 described above in relation to FIGS. 1 and 2.

The method 300 comprises, in step 310, controlling the feed gas supply to supply the flow of air to the first adsorption bed, the first adsorption bed selectively adsorbing the gaseous component from the supplied air to produce a product gas.

Step 310 may thus comprise, for example, opening the first feed valve 210 and the second exhaust valve 226B, while the second feed valve 212 and the first exhaust valve 226A remain closed, as described above in relation to FIG. 2.

In 320, the connection and valve assembly is controlled such that a portion of the product gas produced from the first absorption bed is supplied to the second adsorption bed thereby to release adsorbed gaseous component from the second absorption bed. The released gaseous component is vented from the system in the waste gas.

Blocks 310 and 320 of the flowchart shown in FIG. 5 may, in practice, be performed concurrently.

Step 320 may, for instance, comprise diverting a portion of the product gas from one of the respective adsorption beds 204, 206 to the other adsorption bed 206, 204 via a purge orifice 224, as described above in relation to the exemplary system 200 shown in FIG. 2.

In step 330, the sensor system is used to determine, from the vented waste gas, a measure relating to a flow rate of the waste gas escaping from the system via the vent.

Step 330 may, for example, comprise using the sensor system 232 described above. In particular, the sensor 233 of the sensor system 232 may include a differential pressure sensor for providing an inexpensive and accurate determination of the measure relating to the flow rate of the waste gas escaping from the system 200 via the vent 230.

The method 300 further comprises adjusting 340 at least one parameter relating to an amount of air being alternately supplied to the first adsorption bed and/or to the second adsorption bed based on the measure.

The at least one parameter may be at least one selected from the first time period during which the feed gas supply 202 supplies the flow of air to the first adsorption bed 204, the second time period during which the feed gas supply 202 supplies the flow of air to the second adsorption bed 206, and a feed gas flow rate of the air being supplied to the respective adsorption beds 204, 206 by the feed gas supply 202, as previously described.

Operation of the system 200 may thus be adjusted in order to account for, for example, any differences between the adsorption capacities of the respective first and second adsorption beds 204, 206.

The method 300 may then, for example, continue with the feed gas supply being controlled to supply the flow of air to the second adsorption bed, and so on.

Some or all of the steps of the method 300 may, for instance, be automatically implemented using a controller, as previously described.

EXAMPLES

In a non-limiting example, a commercially available POC (SimplyGo Mini POC from Philips) was equipped with a vent 230 in the exhaust line defined by five exhaust orifices 230A, 230B, 230C, 230D, 230E in parallel, each having a diameter of about 1.4 mm. A differential pressure sensor 233 (Honeywell ASDX015D44R) was connected to this orifice assembly, according to the design schematically depicted in FIG. 3. The overall exemplary system 200 corresponds to that shown in FIG. 2.

Figure 6:
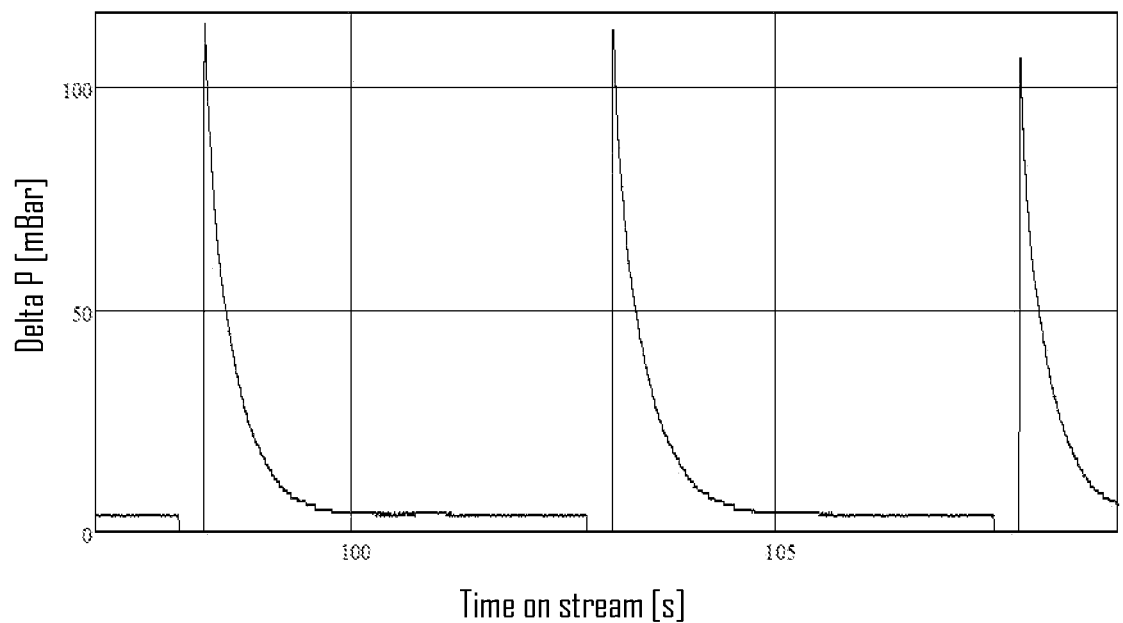
FIG. 6 shows a graph of differential pressure versus time recorded for a system including the exemplary vent and sensor shown in FIG. 3.

The sensor system 232 was coupled to a desktop PC running LabView software by National Instruments, and data acquisition (with 500 Hz sampling rate) and evaluation was performed. FIG. 6 shows a typical waveform of the differential pressure recorded during two half cycles. The waste gas flow rate ($\Phi waste(t)$) was calculated from the measured differential pressure signal ($\Delta p(t)$) using a simple relation (Equation 1) which was found to be valid for exhaust orifices 230A, 230B, 230C, 230D, 230E for releasing the waste gas to the atmosphere.

$$\Phi waste(t) = \Phi 0_{orif}(\Delta p(t)/\text{bar})^{0.513} \quad \text{Equation 1}$$

Figure 7:
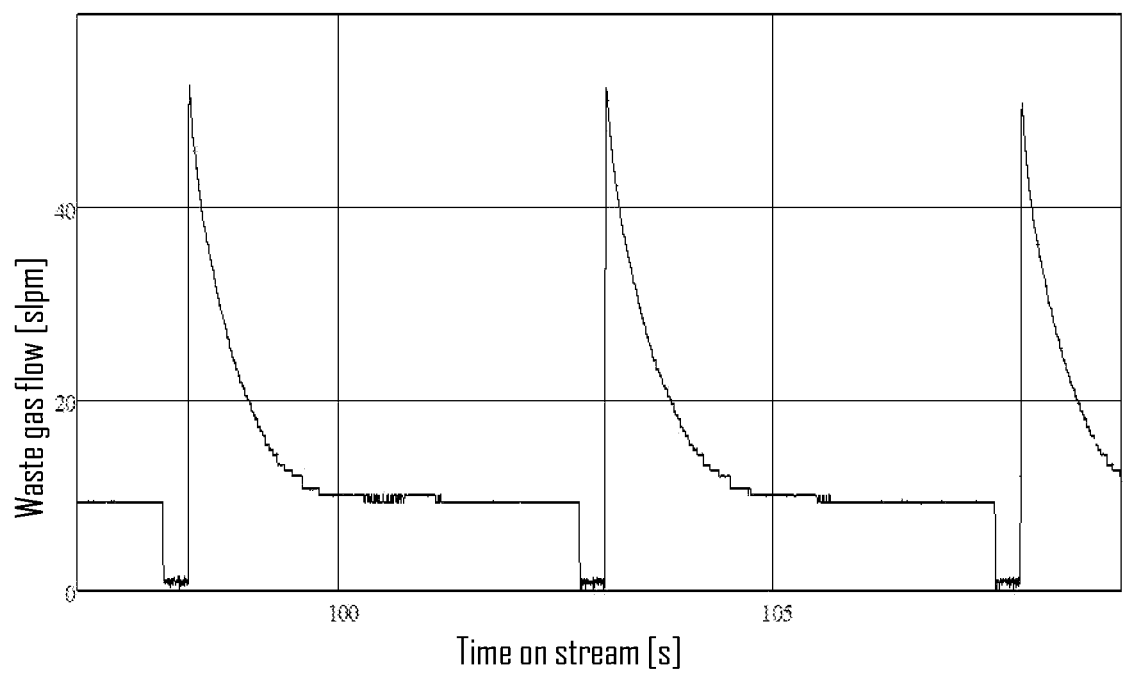
FIG. 7 shows a graph of waste gas flow rate versus time as calculated from the differential pressure measurement shown in FIG. 6.

In Equation 1, the orifice flow constant ($\Phi 0_{orif}$) for the five parallel exhaust orifices 230A, 230B, 230C, 230D, 230E of 1.4 mm diameter was found to be $\Phi 0_{orif}=160$ slpm. (slpm means standard liters per minute; standard conditions being: temperature=298 K; and absolute pressure=1 bar). FIG. 7 shows typical waste gas flow waveforms calculated from the differential pressure measurement of FIG. 6.

By integrating the waste gas flow rates ($\Phi waste(t)$), the waste gas volume for each of the adsorption beds 204, 206 may be obtained, as previously described.

Example 1

In this non-limiting example, the POC was operated in a mode in which the flow of product gas was targeted at 1000 mL/min at a product pulse rate of 21 min$^{-1}$. The experiment was started with the standard initial settings for the first and second time periods: 4.78 s for the first adsorption bed 204 and 4.78 s for the second adsorption bed 206. The first and second time periods being the same is indicative of the respective adsorption capacities of the respective adsorption beds 204, 206 being initially assumed to be the same. The product purity (percentage of oxygen in the product gas) was monitored via an oxygen concentration sensor positioned downstream of the first and second adsorption beds 204, 206.

Measuring the waste gas flow rates (Φwaste(t)), and integrating Φwaste(t) over one half-cycle for the first adsorption bed 204, and the next half-cycle for the second adsorption bed 206 yielded the following waste gas volumes: Vwaste204=1050 mL and Vwaste206=1030 mL. Thus, in operation the first adsorption bed 204 was found to have a larger adsorption capacity than the second adsorption bed 206.

Figure 8:
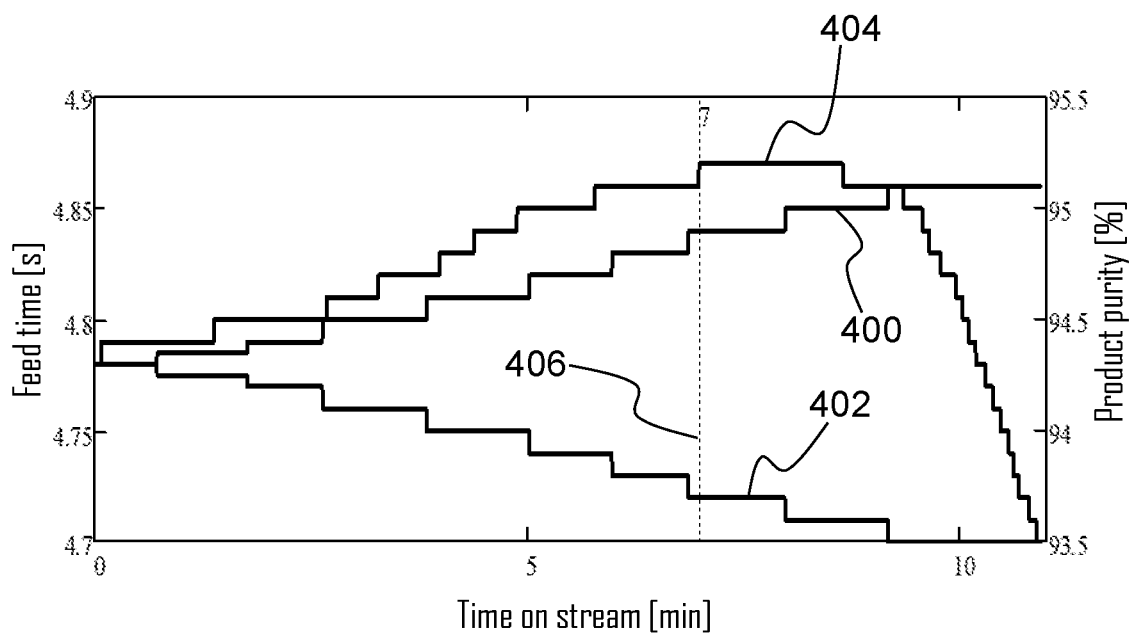
FIG. 8 shows graphs of feed time versus time for respective adsorption beds of an exemplary system, and a graph of product gas purity versus time for the system.

The feed gas supply 202 was subsequently adjusted, as shown in FIG. 8. In particular, during the subsequent 10 minutes, the first time period 400 was incrementally increased in steps of 10 ms, and the second time period 402 was simultaneously decreased by the same incremental steps, thus keeping the average feed time constant. As shown in FIG. 8, during this process, the product purity 404 slowly increased to a maximum and subsequently decreased more rapidly.

By inspection of FIG. 8, the optimum setting 406 of the first and second time periods had apparently been reached at the maximum of product purity, i.e. at 7 minutes, where the first time period was 4.84 s, and the second time period was 4.72 s. The difference between the first and second time periods was thus 120 ms.

Figure 9:
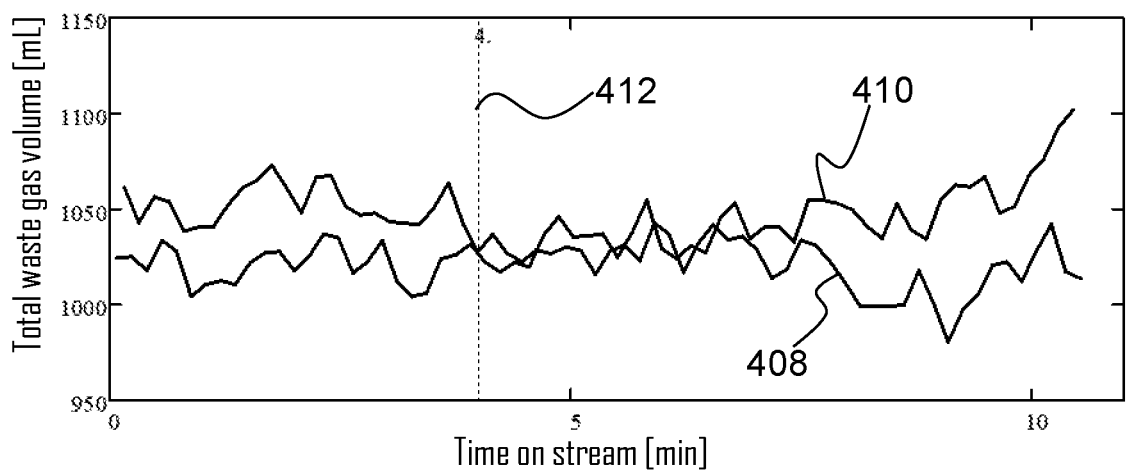
FIG. 9 shows graphs of measured total waste gas volume versus time for respective adsorption beds of the exemplary system to which the graphs of FIG. 8 relate.

However, by inspection of FIG. 9, which shows graphs of the total waste gas volumes 408, 410 of the first adsorption bed 204 and the second adsorption bed 206 respectively, the respective waste gas volumes had become substantially the same as each other much earlier than the "maximum purity" estimate of 7 minutes from FIG. 8. Rather, FIG. 9 points to the respective waste gas volumes becoming identical at about 4 minutes (see dotted line 412), where the first time period was 4.81 s, and the second time period was 4.75 s. The difference between the first and second time periods was thus 60 ms. Further experimentation for about an hour showed that indeed a constant maximum product purity of 95.2% could be maintained using this setting of the first and second time periods.

Thus, it has been surprisingly found that the operating conditions may be adjusted to enable optimization of product purity by adjusting the first/second time periods such that the waste gas flow volumes from both of the adsorption beds 204, 206 become substantially the same as each other.

Moreover, this example indicates that the product purity, as measured using a purity sensor downstream of the first and second adsorption beds 204, 206, takes longer to react to changes in the first/second time period than the measure relating to a flow rate of the waste gas being vented from the system 200.

Furthermore, a quantitative algorithm may be used to estimate the adjustments required to the first and second time periods. As previously noted, the average waste gas volume from the first adsorption bed 204 was 1050 mL, which was thus 2% higher than the average waste gas volume from the second adsorption bed 206, the latter being 1030 mL.

The optimum adjustment of the first time period was from 4.78 s to 4.81 s for the first adsorption bed 204, as explained above in relation to FIG. 9. The second time period was adjusted from 4.78 s to 4.75 s, such that the difference in the first and second time periods increased by 60 ms. The difference in feed times may be independent of the device setting, i.e. independent of the absolute values of the first and second time periods. Therefore, Equations 2A and 3 provide a simple rule to estimate the required change (Δtfeed) in the respective time period:

$$\Delta tfeed204 = 1.5s \cdot \frac{Vwaste204 - Vwaste206}{(Vwaste204 + Vwaste206)/2} \quad \text{Equation 2A}$$

$$\Delta tfeed206 = \Delta tfeed204 \quad \text{Equation 3}$$

In the case of the above non-limiting example, the required change to the first time period (Δtfeed204) would be +30 ms, and the required change to the second time period (Δtfeed206) would be −30 ms.

This demonstrates that determining the respective waste gas volumes (Vwaste204 and Vwaste206 for the first 204 and second 206 adsorption beds respectively) can assist in quickly and reliably symmetrizing the PSA process to optimize product purity (at constant power consumption).

Example 2

Determining the waste gas volumes (Vwaste204 and Vwaste206) can also help in terms of permitting the electrical power input of the system 200 to be reduced whilst maintaining a desired minimum level of product purity.

As a reference, the POC system 200 was initially operated using standard settings: a product pulse rate of 25 min$^{-1}$ at a compressor speed of 1955 RPM, with the first and second time periods being both 4.78 s. A product purity of 94.56% was obtained at a mains power input of 52.44 W. The average waste gas volumes were: Vwaste204=1040 mL and Vwaste206=1007 mL for the first adsorption bed 204 and the second adsorption bed 206 respectively.

The first and second time periods were then adjusted to obtain respective waste gas volumes which were substantially the same as each other: Vwaste204=1026 mL and Vwaste206=1020 mL when the first time period was 4.805 s, and the second time period was 4.755 s. The product purity went up to 95.1% at a mains power input of 52.12 W.

The compressor speed was then lowered to 1800 RPM to obtain a lower feed air inflow and a lower power input. Both waste gas volumes decreased markedly (by about 6%), indicating that the respective adsorption beds 204, 206 were filled to a much lower degree than during standard operation. Thus, it was to be expected that the product purity could not be maintained under these conditions. Therefore, both feed times were subsequently increased until the waste gas volumes returned to values close to their original values: the first time period was 5.098 s, and the second time period was 5.042 s. The waste gas volumes were Vwaste204=1019 mL, and Vwaste206=1009 mL, respectively. The product purity was 93.5% and the mains power input 48.10 W. Thus, a mains power decrease of 8% was realized with respect to the initial reference level of 52.44 W.

Example 3

An experiment was designed in order to test the principles of the present disclosure with adsorption beds 204, 206 having relatively high asymmetry in (nitrogen) adsorption capacity. The second adsorption bed 206 was deliberately degraded such that its adsorption capacity decreased by approximately 20%. This degrading was achieved by continuously flowing ambient air at 20° C. and 52% Relative Humidity (RH) at 4.5 slpm for 148 min through the second adsorption bed 206. In this way, about 6 g of water was introduced into the second adsorption bed 206. The mass of zeolite adsorbent in the second adsorption bed 206 was about 120 g, and the water content of the water vapor filled zone was about 25 wt. %. Thus, introduction of about 6 g water led to an approximately 20% reduction of available nitrogen adsorbent mass.

The POC system 200 was then operated in a mode in which the product flow rate was 660 mL/min, at a product pulse rate of 27 to 29 min$^{-1}$. The experiment was started with the first and second time periods being both 4.094 s.

The respective waste gas flow rates were measured, and integrated over one half-cycle for the first adsorption bed 204, and the next half-cycle for the second adsorption bed 206, as previously described. This yielded: Vwaste204=1011 mL, and Vwaste206=751 mL.

The relative difference of the waste gas volumes was calculated using Equation 4:

$$r\Delta Vwaste = \frac{Vwaste204 - Vwaste206}{(Vwaste204 + Vwaste206)/2} \quad \text{Equation 4}$$

The rΔVwaste was 29.5%.

Figure 10:
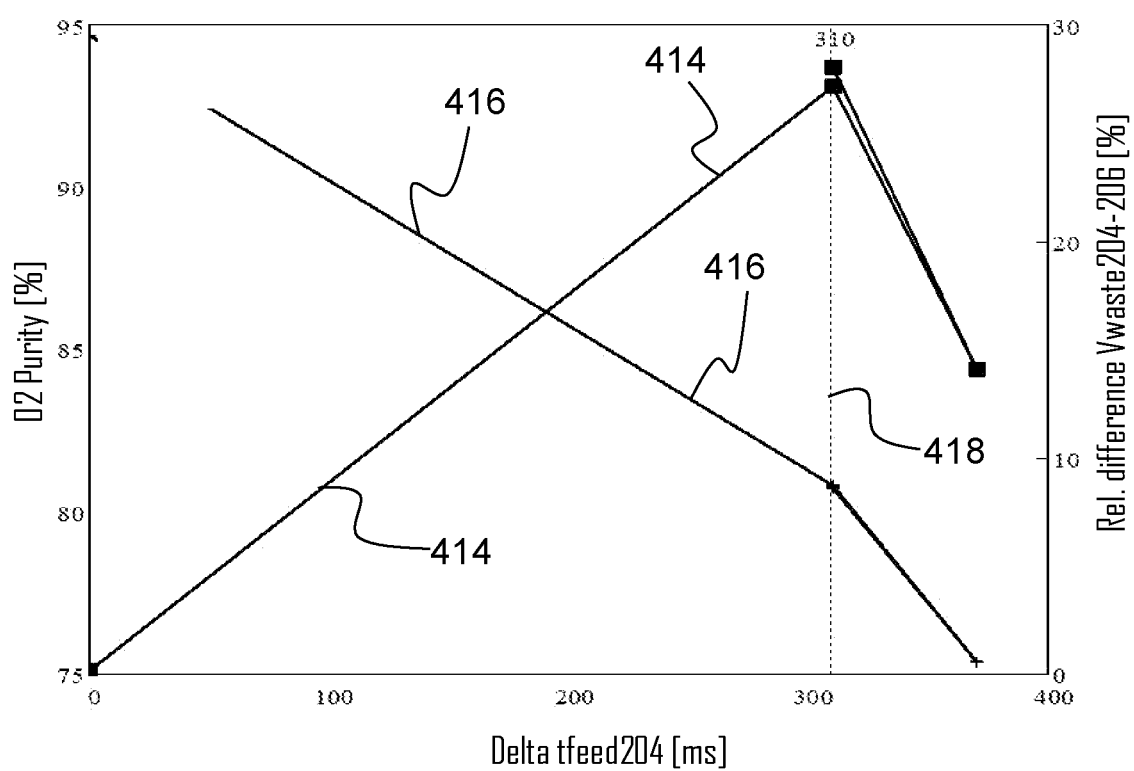
FIG. 10 shows graphs of $O_2$ product purity, and relative difference in waste gas volumes produced by respective adsorption beds as a function of the difference in the time periods during which air is being supplied to the respective adsorption beds.

The first and second time periods were then incrementally adjusted in order to change the difference in the respective time periods (2Δtfeed204), whilst keeping the average of the first and second time periods constant. After each incremental change, the system 200 was permitted to establish a Cyclic Steady State (CS S), and the O$_2$ product purity and the rΔVwaste were measured. The results of this experiment are shown in FIG. 10, in which plot 414 is the product purity as a function of Δtfeed204, and plot 416 is rΔVwaste as a function of Δtfeed204.

Plot 416 indicates that the rΔVwaste is approximately zero at Δtfeed204=380 ms, whereas plot 414 shows that the maximum of product purity 418 is reached at a considerably lower value of Δtfeed204=310 ms. This experiment demonstrates that rΔVwaste need not be fully compensated in order to achieve maximum product purity (e.g. in the case of adsorption beds 204, 206 which have a relatively high degree of asymmetry). Rather, rΔVwaste may be only partially compensated, in this example by approximately 80%.

Additional experiments showed that the first estimation rule derived from Example 1 above may be modified into an averaged rule, which is approximately valid for all values of |rΔVwaste| up to 20%. Writing rΔVwaste(204=206) for the value of rΔVwaste obtained for equal feed times for both sieve beds, the following more general rule applies:

ΔtfeedA=a·rΔVwaste(204=206) to reach rΔVwaste=0;

ΔtfeedA=b·rΔVwaste(204=206) to reach an optimum point of maximum product purity.

The time values a and b may be dependent on the dimensions and operating conditions of the system 200. In (non-limiting) Example 3, a=1.2 s; and b=1.0 s.

Similar, e.g. more accurate, rules may be applicable according to specific operation conditions of an oxygen concentrator, depending, for example, on the product output setting, the age of the adsorption beds 204, 206, etc.

Example 4

Another experiment was conducted with two adsorption beds 204, 206, which had been degraded (as described above in Example 3) by 10% for the first adsorption bed 204, and 20% for the second adsorption bed 206.

The POC system 200 was then operated in a mode in which the product flow rate was 440 mL/min, at a product pulse rate of 25 min$^{-1}$. The experiment was started with the first and second time periods both being 4.094 s, with a compressor speed of 1337 RPM.

The respective waste gas flow rates were measured, and integrated over one half-cycle for the first adsorption bed 204, and the next half-cycle for the second adsorption bed 206. This yielded: Vwaste204=655 mL, and Vwaste206=669 mL. The relative difference of those waste gas volumes was −2.1% (using Equation 4). The O$_2$ product purity was 72.6%.

These results were unexpected, because the adsorption capacity of the first adsorption bed 204 was anticipated to be higher than the capacity of the second adsorption bed 206 (and similarly Vwaste204 should have been higher than Vwaste206). The product purity was also significantly lower than expected, since for these operating conditions at least 80% product purity would be anticipated. It was therefore hypothesized that an air leak at the feed or product side of the first adsorption bed 204 may be present.

Both adsorption beds 204, 206 were carefully remounted, and the experiment was repeated under the same operating conditions. The expected waste gas volumes (Vwaste204=755 mL, and Vwaste206=655 mL; i.e. rΔVwaste=14.2%), and O$_2$ product purity (82.6%) were obtained. This seemed to indicate that an air leak had indeed been present prior to remounting of the adsorption beds 204, 206.

Upon further investigation, a considerable difference was identified between the average waste gas flow rates (Φwaste (t)) without and with an air leak:

without air leak: Φwaste=(Vwaste204+Vwaste206/ (tfeed204+tfeed206)) 8.90 slpm; and with air leak: Φwaste=8.35 slpm.

Figure 11:
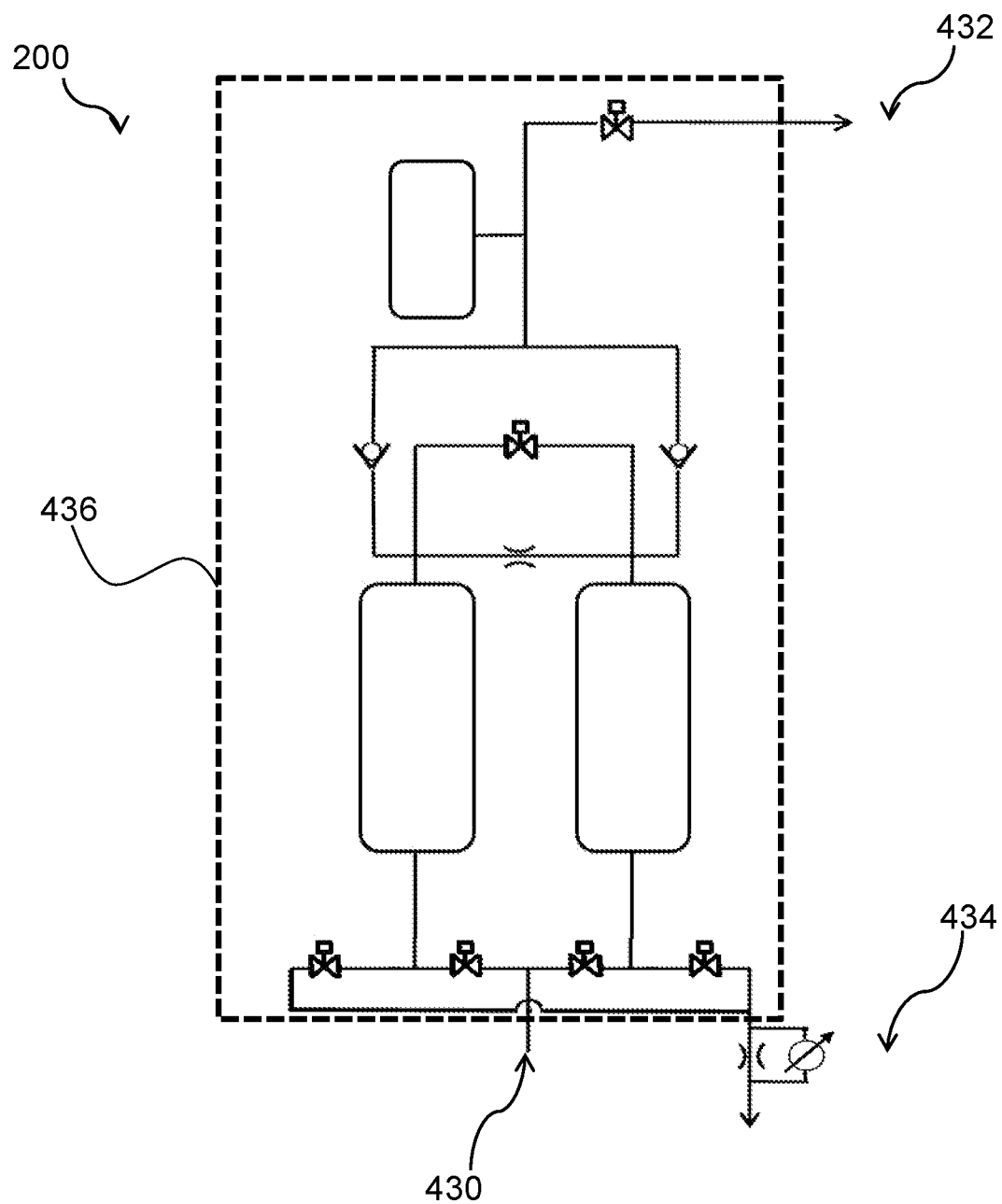
FIG. 11 shows a system according to an example which is annotated for explanation of determination of the average gas flow balance of the system.

This means that the waste gas flow rate with an air leak is about 0.55 slpm lower. Such a large difference should be apparent in the average gas flow balance of the PSA process. FIG. 11 shows the system 200 shown in FIG. 2, but with the air inflow being represented by arrow 430, the product outflow being represented by arrow 432, and the waste gas outflow being represented by arrow 434. The hashed box 436 represents the outer case of the (portable) oxygen concentration system 200.

During CSS, i.e. a stable situation where no net gas is stored or released from the sieve beds during a PSA cycle, the sum of the product outflow (Φprod) and the waste gas outflow (Φwaste) will be equal to the air inflow (Φair). The product outflow (Φprod) may be fixed by the operating setting being used (e.g. the product outflow may be set at 0.44 slpm). The waste gas outflow (Φwaste) may be measured using the sensor system 232, as previously described. The air inflow (Φair) may correspond to the output flow of the compressor (Φcompr), which is a function of the compressor speed, and the delivery pressure (pdeliv) of the product (which may also be measured). The following fit was experimentally obtained:

Φcompr=1.357+0.007015*compressor speed[RPM]− 0.149*pdeliv [psig].

In Example 4, the compressor speed was 1337 RPM, and pdeliv was 9 psig. This gives: Φcompr=9.40 slpm. The average gas flow balances were thus obtained for the with and without air leak scenarios:

without air leak: Φwaste+Φprod=9.34 slpm=Φair≈Φcompr=9.40 slpm, which is approximately equal within the error margin;

with air leak: Φwaste+Φprod=8.79 slpm≠Φair≈Φcompr=9.40 slpm, which clearly indicates a discrepancy.

Therefore, measuring the waste gas outflow may further provide a valuable tool to detect air leaks in the system 200, which may not be apparent from the other monitored signals, such as the delivery pressure.

Whilst the present disclosure primarily concerns an oxygen concentrator system, the same principles may be more generally applied, e.g. to pressure swing adsorptions systems. In such examples, the feed gas may not be limited to air, and the gaseous component need not comprise nitrogen. The first and second adsorption beds may nevertheless selectively adsorb the gaseous component from the feed gas to produce a product gas having a lower concentration of the gaseous component than that in the feed gas.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. An oxygen concentrator system for adsorbing a gaseous component comprising nitrogen from a pressurized flow of air containing the gaseous component, the system comprising:
    a first adsorption bed;
    a second adsorption bed, each of the first and second adsorption beds being for selectively adsorbing the gaseous component from the flow of air to produce a product gas having a higher oxygen concentration than that of the air;
    a feed gas supply configured to supply the flow of air alternately to the first adsorption bed and the second adsorption bed, the feed gas supply being adjustable such as to enable adjustment of at least one parameter relating to an amount of air being alternately supplied to the first adsorption bed and/or to the second adsorption bed;
    a connection and valve assembly between the first and second adsorption beds, the connection and valve assembly being configured such that a portion of the product gas, produced from the respective absorption bed being supplied with the flow of air, is supplied to the other adsorption bed thereby to release adsorbed gaseous component from said other adsorption bed;
    a vent for venting waste gas including said released gaseous component from the system; and
    a sensor system comprising a sensor in fluid communication with the waste gas, the sensor system being configured to determine a measure relating to a flow rate of the waste gas being vented from the system via the vent.

2. The system according to claim 1, comprising a controller for controlling the feed gas supply, the controller being configured to:
    receive said measure from the sensor system; and
    adjust said at least one parameter based on said measure.

3. The system according to claim 2, wherein the controller is configured to, based on said measure, adjust the at least one parameter from a predetermined initial setting.

4. The system according to claim 1, wherein the at least one parameter comprises a first time period during which the feed gas supply supplies the flow of air to the first adsorption bed, and/or a second time period during which the feed gas supply supplies the flow of air to the second adsorption bed.

5. The system according to claim 4, as according to claim 2, wherein the controller is configured to adjust the first time period and the second time period such that substantially the same volume of waste gas is vented when the first adsorption bed is supplied by the feed gas supply during the first time period as when the second adsorption bed is supplied by the feed gas supply during the second time period.

6. The system according to claim 1, wherein the at least one parameter comprises a feed gas flow rate of the air being supplied to the respective adsorption beds by the feed gas supply.

7. The system according to claim 1, wherein the sensor comprises a differential pressure sensor.

8. The system according to claim 1, wherein the vent is defined by one or more exhaust orifice; optionally wherein each of the one or more exhaust orifice has a diameter in the range of 1 mm to 5.5 mm.

9. The system according to claim 1, wherein the connection and valve assembly comprises an equalization valve arrangement configured to transfer pressure from one of the respective adsorption beds which is pressurized to the other adsorption bed prior to the feed gas supply switching to supply said air to said other adsorption bed.

10. The system according to claim 1, further comprising:
    a conduit arranged to carry the product gas downstream away from the first and second adsorption beds; and optionally
    a storage tank for receiving the product gas carried via the conduit and storing the product gas.

11. The system according to claim 1, wherein the first adsorption bed has a first adsorption capacity for the gaseous component, and the second adsorption bed has a second adsorption capacity for the gaseous component, wherein the percentage difference between the first adsorption capacity and the second adsorption capacity is less than or equal to 20%, the respective adsorption capacities being measured under the same conditions.

12. The system according to claim 1, wherein the first adsorption bed comprises a first port and the second adsorption bed comprises a second port, wherein the feed gas supply is configured to supply the flow of air alternately to the first port and the second port.

13. The system according to claim 12, wherein the first adsorption bed comprises a further first port spaced apart from the first port across the first adsorption bed, and the second adsorption bed comprises a further second port spaced apart from the second port across the second adsorption bed, the product gas being released from the first adsorption bed and the second adsorption bed via the further first port and the further second port respectively, wherein the connection and valve assembly is configured such that said portion of the product gas is passed from one of the respective further first and further second ports to the other of the respective further second and further first ports.

14. The system according to claim 1, wherein the system is a portable oxygen concentrator system.

15. A method for operating an oxygen concentrator system for adsorbing a gaseous component comprising nitrogen from a pressurized flow of air containing the gaseous component, the system comprising:
- a first adsorption bed;
- a second adsorption bed;
- a feed gas supply configured to supply the flow of air alternately to the first adsorption bed and the second adsorption bed;
- a connection and valve assembly between the first and second adsorption beds;
- a vent for venting waste gas from the system; and
- a sensor system, the method comprising:
- controlling the feed gas supply to supply the flow of air to the first adsorption bed, the first adsorption bed selectively adsorbing the gaseous component from the supplied air to produce a product gas having a higher oxygen concentration than that of the air;
- controlling the valve assembly such that a portion of the product gas produced from the first absorption bed is supplied to the second adsorption bed thereby to release adsorbed gaseous component from the second adsorption bed, said released gaseous component being vented from the system in the waste gas;
- using the sensor system to determine, from the vented waste gas, a measure relating to a flow rate of the waste gas escaping from the system via the vent; and
- adjusting at least one parameter relating to an amount of air being alternately supplied to the first adsorption bed and/or to the second adsorption bed based on said measure.

* * * * *